United States Patent
Rho et al.

(10) Patent No.: US 7,517,911 B2
(45) Date of Patent: Apr. 14, 2009

(54) 3,4,5-TRIMETHOXY PHENYL-BASED ESTER COMPOUND AND PREPARATION METHOD THEREOF AND WHITENING COSMETIC COMPOSITION CONTAINING THE SAME

(75) Inventors: Ho-Sik Rho, Kyunggi-do (KR);
Jae-Sung Hwang, Kyunggi-do (KR);
Hyun-Jung Choi, Kyunggi-do (KR);
Hyun-Jung Shin, Seoul (KR);
Bae-Hwan Kim, Kyunggi-do (KR);
Eun-Young Lee, Seoul (KR);
Byeong-Gon Lee, Kyunggi-do (KR);
Duck-Hee Kim, Seoul (KR)

(73) Assignee: Amorepacific Corporation, Seoul (KR)

( * ) Notice: Subject to any disclaimer, the term of this patent is extended or adjusted under 35 U.S.C. 154(b) by 642 days.

(21) Appl. No.: 10/490,280

(22) PCT Filed: Sep. 23, 2002

(86) PCT No.: PCT/KR02/01793

§ 371 (c)(1),
(2), (4) Date: Oct. 1, 2004

(87) PCT Pub. No.: WO03/027055

PCT Pub. Date: Apr. 3, 2003

(65) Prior Publication Data

US 2006/0167093 A1    Jul. 27, 2006

(30) Foreign Application Priority Data

Sep. 24, 2001  (KR) ............................... 2001-59048

(51) Int. Cl.
*A61K 31/00*    (2006.01)
*C07C 69/00*    (2006.01)

(52) U.S. Cl. ............................ 514/570; 424/60; 424/55; 560/183

(58) Field of Classification Search ................. 514/570; 424/55, 60; 560/183
See application file for complete search history.

(56) References Cited

U.S. PATENT DOCUMENTS 7,282,522 B2 * 10/2007 Rho et al. ................... 514/575

FOREIGN PATENT DOCUMENTS

| JP | 08-283137 A | 10/1996 |
| JP | 8-283137 A | 10/1996 |
| JP | 09-249544 A | 9/1997 |
| JP | 9-249544 A | 9/1997 |
| KR | 2000-13371 A | 3/2000 |
| KR | 2000-0013371 A | 3/2000 |
| KR | 2001-0037325 A | 5/2001 |
| KR | 2001-37325 A | 5/2001 |

OTHER PUBLICATIONS

Ando, T. et al. (AN 1992:112682, CAPLUS, J. of Hazardous Materials (1991), 28(3), 251-80).*

* cited by examiner

*Primary Examiner*—Sabiha N. Qazi
(74) *Attorney, Agent, or Firm*—Sughrue Mion, PLLC

(57) ABSTRACT

The present invention relates to ester compounds derived from 3,4,5-trimethoxy phenyl acetate, 3,4,5-trimethoxy cinnamate or 3,4,5-trimethoxy hydrocinnamate that are represented by Formula (I), wherein $R_1$ is $CH_2$—, —CH=CH— or $CH_2$—$CH_2$, $R_2$ is thymyl or carvacryl, to methods for preparing them, and to a whitening cosmetic composition containing the ester compounds. Because the ester compounds of the present invention inhibit the generation of melanin, the cosmetic composition can improve the skin pigmentation and can be used for whitening cosmetics.

2 Claims, No Drawings

3,4,5-TRIMETHOXY PHENYL-BASED ESTER COMPOUND AND PREPARATION METHOD THEREOF AND WHITENING COSMETIC COMPOSITION CONTAINING THE SAME

FIELD OF THE INVENTION

The present invention relates to ester compounds derived from 3,4,5-trimethoxy phenyl acetate, 3,4,5-trimethoxy cinnamate or 3,4,5-trimethoxy hydrocinnamate represented by Formula 1, and to methods for preparing the ester compounds and a whitening cosmetic composition containing the same.

[Formula 1]

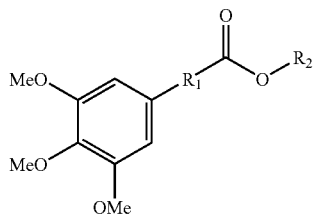

(wherein $R_1$ is —$CH_2$—, —CH=CH— or —$CH_2$—$CH_2$—, $R_2$ is thymyl or carvacryl)

BACKGROUND OF THE INVENTION

The color of a person's skin is determined by the amount of melanin, carotene, hemoglobin or the like, and among them, the melanin is the most important component. Melanin is synthesized in a melanocyte that exists in a basal stratum of skin (epidermis) and transferred to tissues or keratinocytes to reveal the color of the skin. The melanin that exists in an epidermis, which is in the outer position of skin, blocks and absorbs the ultraviolet rays to protect the inner skin organs under the dermis as well as removes free radicals generated in tissues to protect proteins and genes of the tissue.

However, the melanin generated by the stimulus of the inner or outer stress is not easily removed and remains until removed by keratinization of the skin, because melanin is very stable. Therefore, the over-generated melanin is an important source of trouble to make freckles or liver spots. The process of synthesizing a melanin is a kind of polymerization oxidation reaction that uses tyrosine or DOPA as a substrate and uses tyrosinase as an enzyme. When the amount of free radicals increases or inflammation reaction appears in the skin, or when ultraviolet rays hurt the skin, the synthesis of melanin increases.

As materials to inhibit or prevent melanin, polyoxy phenol compounds such as phenol, catechol and resorcinol, kojic acid, tocopherol, ascorbic acid and hydroquinone or the like are known. However, these materials show the anti-melanin effects by inhibiting the activities of the enzymes, and therefore, also show stimuli or toxicity to the skin in addition to the merit of inhibiting the activities of the enzymes.

In particular, hydroxy phenol compounds have such problems as being easily converted to quinone by tyrosinase to cause a harmful toxicity to the tissues.

In addition, the compounds that have anti-oxidation activities have the problems that they are not stable in the cosmetic formulation and easily change colors or denaturalize odors.

Therefore, the present inventors have studied to solve the problems of conventional whitening cosmetics that show stimuli and toxicity to skin, and to enhance the stability of whitening components in the cosmetic formulation. As one solution to the problem, the present inventors have studied to find compounds that can inhibit the synthesis of melanin and show whitening effects without depending on the anti-oxidation activity.

For this, the present inventors focused on gallic acid esters that are prepared from a kind of trihydroxy phenyl compound, gallic acid, and have various and differently positioned hydroxy groups, and also studied whitening effect and toxicity influenced by the position and number of the hydroxy groups in the gallic acid esters. As a result, the present inventors found that gallic acid esters having a protected tri-hydroxy group show excellent whitening effect. In addition, it was proved that whitening effect was obtained only when the compounds connected by ester bonds are thymol or carvacrol.

Based on the above studies, the present inventors prepared ester compounds by reacting 3,4,5-trimethoxy phenyl acetic acid, 3,4,5-trimethoxy cinnamic acid or 3,4,5-trimethoxy hydrocinnamic acid with thymol or carvacrol, and examined their whitening effects. As a result, the present inventors finally found that these esters have excellent effects of inhibiting the melanin synthesis without showing anti-oxidation activities.

In addition, they also found that these esters do not show cell toxicity, denaturalization of colors or odors and instability that conventional whitening agents belonging to anti-oxidation agents show, and when applied to skin, they do not show stimuli, deterioration or denaturalization.

SUMMARY OF THE INVENTION

An object of the present invention is to provide ester compounds derived from 3,4,5-trimethoxy phenyl acetic acid, 3,4,5-trimethoxy cinnamic acid or 3,4,5-trimethoxy hydrocinnamic acid represented by Formula 1.

[Formula 1]

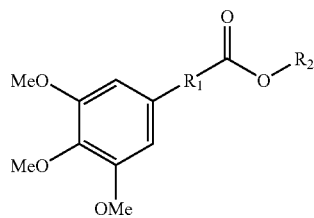

(wherein $R_1$ is —$CH_2$—, —CH=CH— or —$CH_2$—$CH_2$—, $R_2$ is thymyl or carvacryl)

Another object of the present invention is to provide a method for preparing the above ester compounds.

Still another object of the present invention is to provide a whitening cosmetic composition containing the ester compounds.

DETAILED DESCRIPTION OF THE INVENTION

To accomplish the above object, the present invention provides ester compounds represented by Formula 1.

[Formula 1]

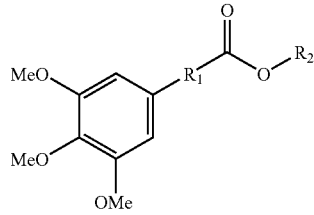

(wherein R$_1$ is —CH$_2$—, —CH=CH— or —CH$_2$—CH$_2$, R$_2$ is thymyl or carvacryl)

In addition, the present invention provides a method for preparing ester compounds by reacting 3,4,5-trimethoxy phenyl acetic acid, 3,4,5-trimethoxy cinnamic acid or 3,4,5-trimethoxy hydrocinnamic acid with thymol or carvacrol, by a method of esterification such as dehydration reaction method using acid catalyst, acid halogenation method, acid anhydride method or active ester method.

Further, the present invention provides a whitening cosmetic composition containing at least one of the ester compounds with an amount of 0.01~20 wt % to the total weight of the cosmetic composition.

Hereinafter, the present invention is described in detail.

The ester compounds of the invention derived from 3,4,5-trimethoxy phenyl acetic acid, 3,4,5-trimethoxy cinnamic acid or 3,4,5-trimethoxy hydrocinnamic acid may be prepared by the following four methods. That is, the methods for preparing ester compounds from 3,4,5-trimethoxy phenyl acetic acid, 3,4,5-trimethoxy cinnamic acid or 3,4,5-trimethoxy hydrocinnamic acid may comprise the followings;

- (A) "Acid catalyst dehydration method", that is, reacting 3,4,5-trimethoxy phenyl acetic acid, 3,4,5-trimethoxy cinnamic acid or 3,4,5-trimethoxy hydrocinnamic acid with thymol or carvacrol under the presence of an acid catalyst to obtain ester compounds;
- (B) "Acid halogenation method", that is, after halogenating 3,4,5-trimethoxy phenyl acetic acid, 3,4,5-trimethoxy cinnamic acid or 3,4,5-trimethoxy hydrocinnamic acid, then reacting it with thymol or carvacrol under the presence of base to obtain ester compounds;
- (C) "acid anhydride method", that is, preparing anhydrous compounds (acid anhydrides) of 3,4,5-trimethoxy phenyl acetic acid, 3,4,5-trimethoxy cinnamic acid or 3,4,5-trimethoxy hydrocinnamic acid, then reacting the above acid anhydrides with thymol or carvacrol to make ester compounds; or
- (D) "active ester method", that is, reacting 3,4,5-trimethoxy phenyl acetic acid, 3,4,5-trimethoxy cinnamic acid or 3,4,5-trimethoxy hydrocinnamic acid with 1,3-dicyclohexylcarbodiimide (DCC) to prepare active ester and reacting it with thymol or carvacrol under the presence of base to make ester compounds.

The methods of preparing the esters are described with reference to the Reaction Formulas.

(A) Acid Catalyst Dehydration Reaction Method

[Reaction Formula 1]

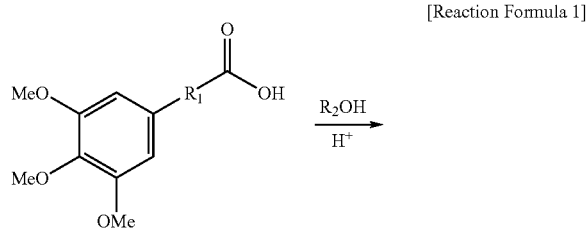

(wherein, R$_1$ is —CH$_2$—, —CH=CH— or —CH$_2$—CH$_2$, R$_2$ is thymyl or carvacryl)

In this method, ester compounds are obtained by reacting 3,4,5-trimethoxy phenyl acetic acid, 3,4,5-trimethoxy cinnamic acid or 3,4,5-trimethoxy hydrocinnamic acid with thymol or carvacrol under the presence of acid catalyst, and then dehydrating the above obtained product. Acids that can be used in this method comprise sulfuric acid, hydrochloric acid, paratoluene sulfonic acid or the like, and the solvents that can be used comprise toluene, benzene, or the like.

(B) Acid Halogenation Method

[Reaction Formula 2]

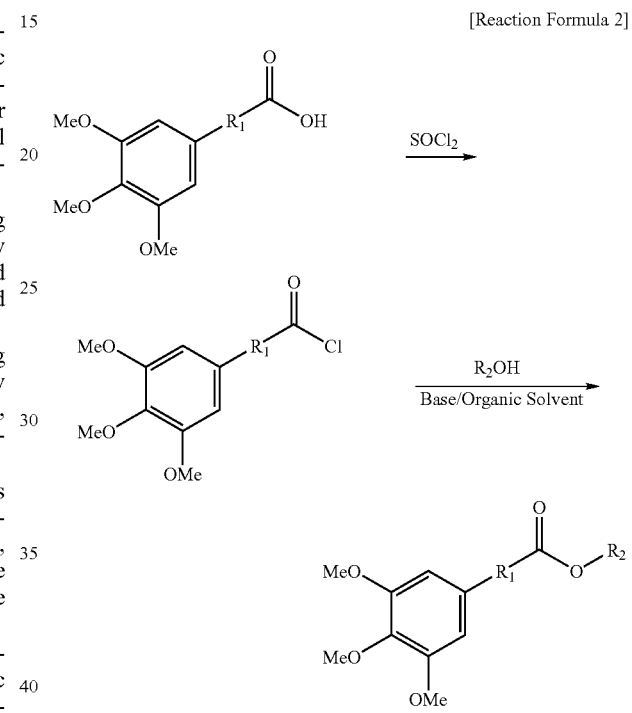

(wherein, R$_1$ is —CH$_2$—, —CH=CH— or —CH$_2$—CH$_2$, R$_2$ is thymyl or carvacryl)

In this method, 3,4,5-trimethoxy phenyl acetic acid, 3,4,5-trimethoxy cinnamic acid or 3,4,5-trimethoxy hydrocinnamic are halogenated by thionyl chlorides, then the thionyl chlorides are reacted with thymol or carvacrol under the presence of base to obtain ester compounds. Bases that can be used in this method comprise dichloromethane, chloroform, carbon tetrachloride, or the like.

(C) Acid Anhydride Method

[Reaction Formula 3]

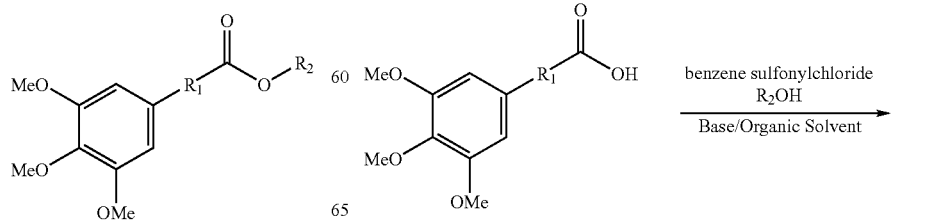

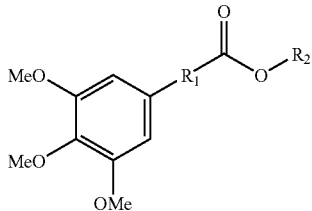

(wherein, R₁ is —CH₂—, —CH=CH— or —CH₂—CH₂—, R₂ is thymyl or carvacryl)

In this method, 3,4,5-trimethoxy phenyl acetic acid, 3,4,5-trimethoxy cinnamic acid or 3,4,5-trimethoxy hydrocinnamic are reacted with benzene sulfonyl chloride to prepare acid anhydrides as intermediates, and the intermediates are reacted with thymol or carvacrol to obtain ester compounds.

(D) Active Ester Method

[Reaction Formula 4]

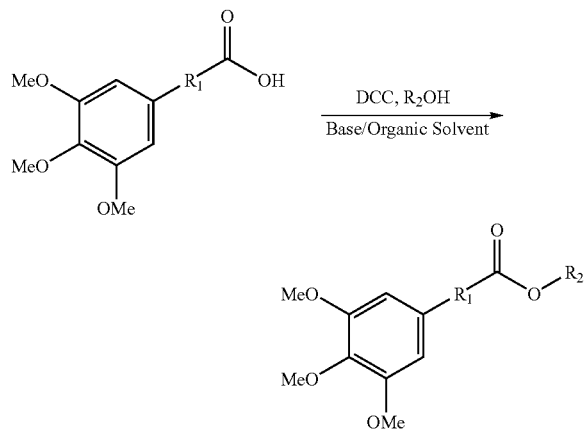

(wherein, R₁ is —CH₂—, —CH=CH— or —CH₂—CH₂—, R₂ is thymyl or carvacryl)

In this method, 3,4,5-trimethoxy phenyl acetic acid, 3,4,5-trimethoxy cinnamic acid or 3,4,5-trimethoxy hydrocinnamic are reacted with 1,3-dicyclohexylcarbodiimide under the presence of base to prepare active esters, and the active esters are reacted with thymol or carvacrol to obtain ester compounds. Wherein, the equivalent ratio of 1,3-dicyclohexylcarbodiimide: thymol or carvacrol is preferably 1:1~1:3.

When the above equivalent ratio is less than 1:1, the amount of desired product is small, and when the equivalent ratio is more than 1:3, there is a problem that remaining thymol or carvacrol not reacted should be removed. Bases that can be used in this method comprise inorganic bases such as sodium hydroxide, potassium hydroxide or potassium carbonate and organic bases such as pyridine or triethylamine; preferably, organic bases are better. Solvents comprise dichloromethane, chloroform or carbon tetrachloride.

The ester compounds derived from 3,4,5-trimethoxy phenylacetic acid, 3,4,5-trimethoxy cinnamic acid or 3,4,5-trimethoxy hydrocinnamic acid, which are represented by Formula 1 and prepared by the above methods comprise, for example;

5-methyl-2-(methylethylphenyl)-2-(3,4,5-trimethoxyphenyl)acetate;

2-methyl-5-(methylethylphenyl)-2-(3,4,5-trimethoxyphenyl)acetate;

5-methyl-2-(methylethyl)phenyl(2E)-3-(3,4,5-trimethoxyphenyl)-2-propanoate;

2-methyl-5-(methylethyl)phenyl(2E)-3-(3,4,5-trimethoxyphenyl)-2-propanoate;

5-methyl-2-(methylethyl)phenyl-3-(3,4,5-trimethoxyphenyl)propanoate;

2-methyl-5-(methylethyl)phenyl-3-(3,4,5-trimethoxyphenyl)propanoate.

The ester compounds derived from 3,4,5-trimethoxy phenylacetic acid, 3,4,5-trimethoxy cinnamic acid or 3,4,5-trimethoxy hydrocinnamic acid, which are represented by Formula 1 and prepared by the above methods, may be used as an active component in a whitening cosmetic composition. The amount of the ester compounds in the whitening cosmetic composition is controlled considering the whitening effect and stability of formulation, and a preferable amount is 0.01~20.0 wt % to the total amount of the cosmetic composition. The formulation of the cosmetics is not restricted, and may be cream, lotion, toilet lotion, skin conditioner, massage cream or essence.

The cosmetic composition of the present invention may contain other preferable components according to the type of the formulation, and a person skilled in the art may easily take other components and control the amounts to be added. For a more enhanced whitening effect, conventional whitening components may be added together with the ester compounds derived from 3,4,5-trimethoxy phenylacetic acid, 3,4,5-trimethoxy cinnamic acid or 3,4,5-trimethoxy hydrocinnamic acid. The kinds and amounts of the additionally added whitening components are well known to a person skilled in the art.

DESCRIPTION Of PREFERRED EMBODIMENTS

Hereinafter, the preparation and the use of the ester compounds derived from 3,4,5-trimethoxy phenyl acetic acid, 3,4,5-trimethoxy cinnamic acid or 3,4,5-trimethoxy hydrocinnamic acid of the present invention is described more specifically with reference to the examples. However, the scope of the present invention is not restricted thereto.

EXAMPLE 1

Preparation of 5-methyl-2-(methylethylphenyl)-2-(3,4,5-trimethoxyphenyl)acetate (Method A)

3,4,5-trimethoxy phenyl acetic acid (9.5 g, 0.042 mol) and thymol (6.3 g, 0.042 mol) were dissolved in 200 ml of toluene, and a catalytic amount of paratoluene sulfonic acid was added then refluxed for 5 hours. After the reaction was completed, reaction solution was condensed, and 500 ml of ethyl acetate was added to dissolve the condensed reaction mixture. The resultant was washed with distilled water twice, dried with anhydrous sodium sulfate, then filtered and condensed, and finally proceeded to column chromatography to obtain 10.5 g (Yield=70%) of white solid state of the object product.

TLC (ethyl acetate:hexane=1:2) $R_f$=0.52 $^1$H NMR (CDCl₃, δ): 7.18(d,1H,J=7.8 Hz), 7.01(d,1H,J=7.8 Hz), 6.81 (s,1H), 6.22(s,2H), 3.86(s,6H), 3.85(s,3H), 3.79(s,2H), 2.80 (m,1H), 2.29(s,3H), 1.08(d,6H,J=6.9 Hz).

(Method B)

3,4,5-trimethoxy phenyl acetic acid (9.5 g, 0.042 mol) was added slowly to the thionyl chloride (15 g, 0.126 mol) cooled to 0° C., and warmed to room temperature, then stirred for 3 hours. Residual thionyl chloride was distilled out to obtain 3,4,5-trimethoxy phenyl acetic acid chloride (10.3 g, 0.042 mol). Thymol (6.3 g, 0.042 mol) and triethylamine (6.4 g, 0.063 mol) were dissolved in 200 ml of dichloromethane and stirred, and then the above 3,4,5-trimethoxy phenyl acetic acid chloride (10.3 g) dissolved in 50 ml of dichloromethane was added thereto drop by drop. After the reaction was completed, reaction solution was condensed, and 500 ml of ethyl acetate was added to dissolve the reaction mixture. The resultant was washed with distilled water twice, dried with anhydrous sodium sulfate, then filtered and condensed, and finally proceeded to column chromatography to obtain 9.0 g (Yield=60%) of white solid state of the object product.

TLC (ethyl acetate:hexane=1:2) $R_f$=0.52 $^1$H NMR(CDCl$_3$, δ): 7.18(d,1H,J=7.8 Hz), 7.01(d,1H,J=7.8 Hz), 6.81(s,1H), 6.22(s,2H), 3.86(s,6H), 3.85(s,3H), 3.79(s,2H), 2.80(m,1H), 2.29(s,3H), 1.08(d,6H,J=6.9 Hz).

(Method C)

3,4,5-trimethoxy phenyl acetic acid (9.5 g, 0.042 mol) was dissolved in pyridine and stirred while adding benzene sulfonyl chloride (7.4 g, 0.042 mol) drop by drop at 0° C. After 3 hours of stirring, thymol (6.3 g, 0.042 mol) dissolved in pyridine was added drop by drop. After the reaction was completed, pyridine was distilled out, and 500 ml of ethyl acetate was added to dissolve the reaction mixture. The resultant was washed with distilled water twice, dried with anhydrous sodium sulfate, then filtered and condensed, and finally proceeded to column chromatography to obtain 12.7 g (Yield=85%) of white solid state of the object product.

TLC (ethyl acetate:hexane=1:2) $R_f$=0.52 $^1$H NMR (CDCl$_3$, δ): 7.18(d,1H,J=7.8 Hz), 7.01(d,1H,J=7.8 Hz), 6.81 (s,1H), 6.22(s,2H), 3.86(s,6H), 3.85(s,3H), 3.79(s,2H), 2.80 (m,1H), 2.29(s,3H), 1.08(d,6H,J=6.9 Hz).

(Method D)

3,4,5-trimethoxy phenyl acetic acid (9.5 g, 0.042 mol) and 1,3-dicyclohexylcarboimide (DCC) (8.6 g, 0.042 mol) were dissolved in 200 ml of dichloromethane, and stirred for 2 hours, then thymol (6.3 g, 0.042 mol) and triethylamine (6.4 g, 0.063 mol) were added together. After 4 hours of stirring, the reaction solution was condensed, and 500 ml of ethyl acetate was added to dissolve the reaction mixture. The resultant was washed with distilled water twice, dried with anhydrous sodium sulfate, then filtered and condensed, and finally proceeded to column chromatography to obtain 10.5 g (Yield=70%) of white solid state of the object product.

TLC (ethyl acetate:hexane=1:2) $R_f$=0.52 $^1$H NMR(CDCl$_3$, δ): 7.18(d,1H,J=7.8 Hz), 7.01(d,1H,J=7.8 Hz), 6.81(s,1H), 6.22(s,2H), 3.86(s,6H), 3.85(s,3H), 3.79(s,2H), 2.80(m,1H), 2.29(s,3H), 1.08(d,6H,J=6.9 Hz).

EXAMPLE 2

Preparation of 2-methyl-5-(methylethylphenyl)-2-(3, 4,5-trimethoxyphenyl)acetate Same procedure as described in Method C of Example 1 was performed except that carvacrol was used instead of thymol, and 10.1 g (Yield=70%) of white solid state of the object product was obtained.

TLC (ethyl acetate:hexane=1:2) $R_f$=0.47 $^1$H NMR(CDCl$_3$, δ): 7.15(d,1H,J=7.8 Hz), 7.00(d,1H,J=7.8 Hz), 6.83(s,1H), 6.63(s,2H), 3.87(s,6H), 3.85(s,3H), 3.80(s,2H), 2.83(m,1H), 2.01(s,3H), 1.22(d,6H,J=6.9 Hz).

EXAMPLE 3

Preparation of 5-methyl-2-(methylethyl)phenyl(2E)-3-(3,4,5-trimethoxyphenyl)-2-propanoate Same procedure as described in Method C of Example 1 was performed except that 3,4,5-trimethoxy cinnamic acid was used instead of 3,4,5-trimethoxy phenyl acetic acid, and 12 g (Yield=76%) of white solid state of the object product was obtained.

TLC (ethyl acetate:hexane=1:4) $R_f$=0.50 $^1$H NMR(CDCl$_3$, δ): 7.81(d,1H,J=15.9 Hz), 7.22(d,1H,J=7.5 Hz), 7.07(d,1H, J=7.5 Hz), 6.88(s,1H), 6.83(s,2H), 6.71(d,1H,J=15.9 Hz), 3.91(s,3H), 3.90(s,6H), 3.01(m,1H), 2.33(s,3H), 1.21(d,6H, J=6.9 Hz).

EXAMPLE 4

Preparation of 2-methyl-5-(methylethyl)phenyl(2E)-3-(3,4,5-trimethoxyphenyl)-2-propanoate Same procedure as described in Method C of Example 1 was performed except that 3,4,5-trimethoxy cinnamic acid was used instead of 3,4,5-trimethoxy phenyl acetic acid, and except that carvacrol was used instead of thymol. As a result, 13 g (Yield=82%) of white solid state of the object product was obtained.

TLC (ethyl acetate:hexane=1:4) $R_f$=0.51 $^1$H NMR(CDCl$_3$, δ): 7.82(d,1H,J=15.9 Hz), 7.20(d,1H,J=7.5 Hz), 7.03(d,1H, J=7.5 Hz), 6.94(s,1H), 6.82(s,2H), 6.71(d,1H,J=15.9 Hz), 3.91 (s,3H), 3.90(s,6H), 2.92(m, 1H), 2.18(s,3H), 1.25(d,6H, J=6.9 Hz).

EXAMPLE 5

Preparation of 5-methyl-2-(methylethyl)phenyl-3-(3, 4,5-trimethoxyphenyl)propanoate Same procedure as described in Method C of Example 1 was performed except that 3,4,5-trimethoxy hydro cinnamic acid was used instead of 3,4,5-trimethoxy phenyl acetic acid, and 12 g (Yield=76%) of white solid state of the object product was obtained.

TLC (ethyl acetate:hexane=1:4) $R_f$=0.50 $^1$H NMR(CDCl$_3$, δ): 7.19(d,1H,J=7.5 Hz), 7.02(d,1H,J=7.5 Hz), 6.69(s,1H), 6.43(s,2H), 3.94(s,3H), 3.93(s,6H), 3.04(m,2H), 2.97(m, 2H), 2.80(m,2H), 2.31(s,3H), 1.20(d,6H,J=6.9 Hz).

EXAMPLE 6

Preparation of 2-methyl-5-(methylethyl)phenyl-3-(3, 4,5-trimethoxyphenyl)propanoate Same procedure as described in Method C of Example 1 was performed except that 3,4,5-trimethoxy hydro cinnamic acid was used instead of 3,4,5-trimethoxy phenyl acetic acid, and except that carvacrol was used instead of thymol. As a result, 13 g (Yield=82%) of white solid state of the object product was obtained.

TLC (ethyl acetate:hexane=1:4) $R_f$=0.51 $^1$H NMR(CDCl$_3$, δ): 7.18(d,1H,J=7.5 Hz), 7.01(d,1H,J=7.5 Hz), 6.69(s,1H), 6.42(s,2H), 3.95(s,3H), 3.93(s,6H), 3.04(m,2H), 2.97(m, 2H), 2.76(m,2H), 2.31 (s,3H), 1.20(d,6H,J=6.9 Hz).

EXPERIMENTAL EXAMPLE 1

Melanin-inhibiting Effect in the Melanocytes

The generation of melanin in the cell when the compounds of Examples 1~6 were added was measured by the Dooley method. As the cells, Mel-Ab cells that are originated from pigment cells (melanocytes) of C57BL/6 were used. The cells were cultured in a DMEM culture medium containing 10% of bovine placental serum, 100 nM of 12-O-tetradecanoyl phobol-13-acetate, and 1 nM of cholera toxin, under the condition of 37° C. and 5% $CO_2$. The above cultured Mel-Ab cells were isolated by 0.25% of trypsin-EDTA, and the same amounts of cells ($1\times10^5$ cells/well) were planted to 24-well plates respectively and cultured. From the second day, the culture medium was replaced with other culture medium further containing 10 ppm of the ester compounds prepared in the Examples 1~6, for three days.

For reference, tests and measurements were performed for kojic acid that is a well known whitening agent, and for 3,4,5-trimethoxy phenylacetic acid, 3,4,5-trimethoxy cinnamic acid, 3,4,5-trimethoxy hydrocinnamic acid, thymol and carvacrol, repetively.

After five days, 1N of NaOH was treated to the cell cultured wells to dissolve out the melanin generated in the cells. The amount of melanin was measured by measuring the absorbance at 400 nm, and the melanin generation ratio (%) was calculated by comparing with those from the cells cultured in a culture medium not containing any compound of the present invention. The results are shown in Table 1.

TABLE 1

| Material added to culture medium | Melanin generation ratio (%) |
|---|---|
| Kojic acid | 88.0 |
| 3,4,5-trimethoxy phenylacetic acid | 95.8 |
| 3,4,5-trimethoxy cinnamic acid | 96.3 |
| 3,4,5-trimethoxy hydrocinnamic acid | 92.5 |
| Thymol | 94.5 |
| Carvacrol | 91.5 |
| Example 1 | 47.8 |
| Example 2 | 51.2 |
| Example 3 | 45.6 |
| Example 4 | 58.9 |
| Example 5 | 50.0 |
| Example 6 | 48.1 |

As shown in Table 1, the ester compounds of Examples 1~6 which are derived from 3,4,5-trimethoxy phenylacetic acid, 3,4,5-trimethoxy cinnamic acid and 3,4,5-trimethoxy hydrocinnamic acid have excellent ability to inhibit the generation of melanin in the cell.

EXPERIMENTAL EXAMPLE 2

Whitening Effect on the Human Skin

The brachia of twelve (12) healthy volunteers (males) were attached with opaque tape having 1.5 cm diameter holes, and then irradiated with UVB (ultraviolet rays B) in 1.5~2 times the intensity of the minimum amount to form erythema for each volunteer, to induce pigmentation. After irradiating the UVB, 1% diluted solutions of the ester compounds of Examples 1~6 (solvent was 1,3-butyleneglycol:ethanol=7:3) were applied on the above treated brachia for ten (10) weeks (the above 1% diluted solution was not applied on one brachium), and the colors of the skins thereof were measured by Chromameter CR2002 (manufactured by Minolta; Japan) per every one week. The difference of "L", that is, "$\Delta$ L", the amount of the increase of brightness of skin compared with those not applied with diluted solution, was measured. For reference, measurements for the cases that 3% kojic acid and vehicle (solvent) were applied were performed. The results are shown in Table 2.

TABLE 2

| Materilal | Increase of brightness of skin ($\Delta$ L) |
|---|---|
| Vehicle | 0.50 ± 0.15 |
| Kojic acid | 0.99 ± 0.11 |
| Example 1 | 1.71 ± 0.25 |
| Example 2 | 1.51 ± 0.13 |
| Example 3 | 1.38 ± 0.11 |
| Example 4 | 1.22 ± 0.18 |
| Example 5 | 1.40 ± 0.12 |
| Example 6 | 1.49 ± 0.11 |

As shown in table 2, the ester compounds of Examples 1~6 showed more increases in the brightness of skin compared with that of a conventional whitening agent, kojic acid, which proves that the ester compounds of the present invention have excellent whitening effects.

Formulations 1~6 and Comparative Formulation 1

To evaluate the clinical whitening effects of formulations containing the ester compounds of the present invention, cream formulations were prepared as shown in Table 3. After weighing and mixing the components of each group A, B and C respectively, the components of group A were added to the mixture of group B and first emulsified in a homomixer, then the components of group C were added thereto and second emulsified, then followed by stirring and cooling to obtain the desired product. In the followings, "Form." means "formulation" and "Comp." means "comparative".

TABLE 3

| | Component | Wt % | | | | | | | |
|---|---|---|---|---|---|---|---|---|---|
| | | Form. 1 | Form. 2 | Form. 3 | Form. 4 | Form. 5 | Form. 6 | Comp. Form. 1 | Control Form. |
| (A) | Stearyl alcohol | 10.0 | 10.0 | 10.0 | 10.0 | 10.0 | 10.0 | 10.0 | 10.0 |
| | Polysolbate 60 | 1.2 | 1.2 | 1.2 | 1.2 | 1.2 | 1.2 | 1.2 | 1.2 |
| | Sorbitan Cesquioleate | 0.6 | 0.6 | 0.6 | 0.6 | 0.6 | 0.6 | 0.6 | 0.6 |
| | Fluid Paraffin | 10.0 | 10.0 | 10.0 | 10.0 | 10.0 | 10.0 | 10.0 | 10.0 |
| | Squalene | 5.0 | 5.0 | 5.0 | 5.0 | 5.0 | 5.0 | 5.0 | 5.0 |
| | Preservative | 0.2 | 0.2 | 0.2 | 0.2 | 0.2 | 0.2 | 0.2 | 0.2 |
| | Triethanol amine | 0.2 | 0.2 | 0.2 | 0.2 | 0.2 | 0.2 | 0.2 | 0.2 |

TABLE 3-continued

| | | Wt % | | | | | | |
|---|---|---|---|---|---|---|---|---|
| Component | | Form. 1 | Form. 2 | Form. 3 | Form. 4 | Form. 5 | Form. 6 | Comp. Form. 1 | Control Form. |
| (B) | Glycerin | 5.0 | 5.0 | 5.0 | 5.0 | 5.0 | 5.0 | 5.0 | 5.0 |
| | Ethanol | 2.0 | 2.0 | 2.0 | 2.0 | 2.0 | 2.0 | 2.0 | 2.0 |
| | Distilled water | to 100 | to 100 | to 100 | to 100 | to 100 | to 100 | to 100 | to 100 |
| (C) | Carboxyvinyl polymer | 0.2 | 0.2 | 0.2 | 0.2 | 0.2 | 0.2 | 0.2 | 0.2 |
| | Example 1 | 1.0 | — | — | — | — | — | — | — |
| | Example 2 | — | 1.0 | — | — | — | — | — | — |
| | Example 3 | — | — | 1.0 | — | — | — | — | — |
| | Example 4 | — | — | — | 1.0 | — | — | — | — |
| | Example 5 | — | — | — | — | 1.0 | — | — | — |
| | Example 6 | — | — | — | — | — | 1.0 | — | — |
| | Kojic acid | — | — | — | — | — | — | 1.0 | — |
| | Fragrance | q.s. | q.s. | q.s. | q.s. | q.s. | q.s. | q.s. | q.s. |

EXPERIMENTAL EXAMPLE 3

Clinical Test for Whitening Effect

The Formulations 1~6 containing the ester compounds of the present invention and Comparative Formulation 1 containing conventional whitening agent (kojic acid) were applied on the faces of eighty (80) volunteers, who have a problem of pigmentation such as freckles on the face, once in the morning and once in the evening for three (3) months. As for a control group, same test was performed by using the formulation containing only solvents.

<Standards for Measurement>

After using the formulations, measurement was performed according to the standards for measuring improvement of pigmentation. The average values of each group comprising ten (10) volunteers are shown in Table 4.

Excellent (3): Pigmentation was seldom detected.
Good (2): Pigmentation was faded away a lot.
Better than normal (1): Pigmentation was faded away.
No effect (0): Pigmentation was not faded away.

TABLE 4

| Material | Average value of whitening |
|---|---|
| Solvent (vehicle) | 0.4 ± 0.12 |
| Comp. Formulation 1 | 1.4 ± 0.21 |
| Formulation 1 | 2.1 ± 0.22 |
| Formulation 2 | 2.4 ± 0.18 |
| Formulation 3 | 2.0 ± 0.13 |
| Formulation 4 | 1.7 ± 0.17 |
| Formulation 5 | 2.1 ± 0.15 |
| Formulation 6 | 1.9 ± 0.19 |

As shown in Table 4, it is proved that the ester compounds of the present invention have excellent whitening effects.

EXPERIMENTAL EXAMPLE 4

Test for Skin Irritation on Animals

1) Testing Method

The hairs on the backs of six (6) healthy male rabbits were removed. After making areas of 2.5 cm×2.5 cm on the left and right sides of the back of each rabbit, nothing was applied on the left area of the back as control area, and 1% diluted solutions of the ester compounds of Examples 1~6 (solvent was 1,3-butyleneglycol:ethanol=7:3) were applied on the right area of the back of the rabbits with an amount of 0.5 ml, one compound for each rabbit respectively. Irritations such as erythema, rash or edema were measured 24 hours and 72 hours after the application. The evaluation was graded according to "Standard for toxicity of pharmaceuticals et al" as shown in Table 5. In addition, the degree of irritation was determined according to the conventional, "P.I.I." (Primary Irritation Index) of Draize, and the results are shown in Table 6.

TABLE 5

| Degree of skin irritation | point |
|---|---|
| 1) Formation of erythema and rash | |
| No erythema | 0 |
| Mild erythema (not noticeable with the naked eyes) | 1 |
| Clear erythema | 2 |
| Middle level of intense erythema | 3 |
| Dark red intense erythema and rash | 4 |
| 2) Formulation of edema | |
| No edema | 0 |
| Mild edema (not noticeable by the naked eyes) | 1 |
| Clear edema (clearly distinguished) | 2 |
| Middle level of intense edema (swelling about 1 mm) | 3 |
| Intense edema (swelling more than 1 mm and the swelling is extended to outer area) | 4 |

TABLE 6

| Material | P.I.I. | Determination |
|---|---|---|
| Example 1 | 0.375 | No irritation |
| Example 2 | 0.345 | No irritation |
| Example 3 | 0.375 | No irritation |
| Example 4 | 0.350 | No irritation |
| Example 5 | 0.375 | No irritation |
| Example 6 | 0.315 | No irritation |

From the results of table 6, it is proved that the ester compounds of the Examples 1~6 do not have irritation.

EXPERIMENTAL EXAMPLE 5

Test for Radiation Toxicity

The hairs on the backs of ten (10) guinea pigs were removed. After fixing the pigs, the back was divided into six (6) areas each having 2.0 cm×2.0 cm area, three (3) areas on the left side and three (3) on the right side. Right side areas were control areas prevented from being radiated, and left side areas were radiation areas. 1% (w/v) diluted solutions of ester compounds of Examples 1~6 were applied thereto with an equal amount of 50 μl respectively, while using vehicle (1,3-butyleneglycol:ethanol=7:3) as a negative control, and using 0.1% 8-MOP(methoxypsoralene) as a positive control. After 30 minutes later, left sides of the back of the pig was shielded from light by aluminum foil, and UVA(320~380 nm) was radiated from 10 cm distant with an final energy of 15J/cm$^2$ by using ultraviolet radiation device (waldmann). The skin of the guinea pig was observed after 24, 48 and 72 hours later. The irritation was graded as shown in table 5 with 0~4 grades according to the intensity of the erythema and edema, and the sum was calculated. In the evaluation, the maximum value of the measurement that performed after 24, 48 and 72 hours later was chosen, and then the Irritation Index of an animal skin was calculated according to mathematical formula 1, and finally, the Radiation Toxicity Index was calculated according to mathematical Formula 2.

Irritation Index of an animal skin=(Σ maximum value of erythema index+Σ maximum value of edema index)/number of animals       [Mathematical Formula 1]

Radiation Toxicity Index=(Irritation Index of an animal skin in an area of UV radiation)−(Irritation Index of an animal skin in an area UV non-radiation)       [Mathematical Formula 2]

TABLE 7

| Material | Radiation Toxicity Index | Determination |
|---|---|---|
| Example 1 | 0 | Radiation Non-Toxic |
| Example 2 | 0 | Radiation Non-Toxic |
| Example 3 | 0 | Radiation Non-Toxic |
| Example 4 | 0 | Radiation Non-Toxic |
| Example 5 | 0 | Radiation Non-Toxic |
| Example 6 | 0 | Radiation Non-Toxic |

From the results of Table 7, it is proved that the ester compounds of the Examples 1~6 do not have radiation toxicity because they have zero (0) grade of Radiation Toxicity Index.

EXPERIMENTAL EXAMPLE 6

Ames Test

Reverse mutation test using *Salmonella Typhimurium* TA98, TA100 was performed according to a conventional method. Under the condition of using the compounds of the present invention, test samples showed negative, and mutation was not induced.

EXPERIMENTAL EXAMPLE 7

Test for Application to Human Skin

Thirty (30) male and female volunteers with average age of 24.8 who had an experience of skin irritation underwent the following test according to CTFA Guideline (The Cosmetic, Toiletry and Fragrance Association, Inc. Washington, D.C. 20036, 1991). Each of the ester compounds of Examples 1~6 were dissolved in a patch base shown in Table 8 to be 1% concentration respectively, to prepare test samples. 20 μl of each test sample was dropped in a Finn Chamber to make a patch, and the patch was attached to antebrachial skin (test region) and fixed with micro tape. The patch was attached for 24 hours, and after removing the patch, the test region was checked with marking pen, and then the region was observed after 1 and 24 hours. The irritation reaction in the skin was evaluated as shown in Table 9, and the results are shown in Table 10.

TABLE 8

| Component | CTFA | Content |
|---|---|---|
| Oil and wax | Gylceryl stearate | 1.50 |
|  | Squalene | 7.00 |
|  | Mineral oil | 7.00 |
|  | Cetyl alcohol | 1.20 |
| surfactant | Sorbitan stearate | 0.30 |
|  | Polysolbate 60 | 1.00 |
| Thickner | Carbomer | 0.12 |
| Polyol | Glycerin | 10.00 |
| Water | Distilled water | To 100 |

TABLE 9

| Grade | Mark | Standard of determination |
|---|---|---|
| 0 | − | No visible reactions |
| 1 | ± | Mild erythema |
| 2 | + | Intense erythema |
| 3 | ++ | Intense erythema with edema |
| 4 | +++ | Intense erythema with edema &vesicle |

TABLE 10

| | The number of volunteers having reaction | | | | | | | | | | Average reaction |
|---|---|---|---|---|---|---|---|---|---|---|---|
| | 24 hours later | | | | | 48 hours later | | | | | |
| Material | − | ± | + | ++ | +++ | − | ± | + | ++ | +++ | (n = 30) |
| Example 1 | 28 | 2 | 0 | 0 | 0 | 30 | 0 | 0 | 0 | 0 | 0.83 |
| Example 2 | 30 | 0 | 0 | 0 | 0 | 29 | 1 | 0 | 0 | 0 | 0.42 |
| Example 3 | 30 | 0 | 0 | 0 | 0 | 30 | 0 | 0 | 0 | 0 | 0.00 |
| Example 4 | 29 | 1 | 0 | 0 | 0 | 30 | 0 | 0 | 0 | 0 | 0.42 |
| Example 5 | 30 | 0 | 0 | 0 | 0 | 30 | 0 | 0 | 0 | 0 | 0.00 |
| Example 6 | 30 | 0 | 0 | 0 | 0 | 30 | 0 | 0 | 0 | 0 | 0.00 |

Average reaction = {(grade × number of volunteers of each reaction) × 100}/ {(maximum grade) × (total number of volunteers) × (the number of test)}

As shown in Table 10, the cosmetic composition of the present invention has an average irritation reaction value of 0~0.83, which is less than that of the non-irritation standard value "1.0", and therefore, the cosmetic composition of the present invention is very safe for use.

USEFULLNESS IN THE INDUSTRY

As seen above, ester compounds of the present invention derived from 3,4,5-trimethoxy phenylacetic acid, 3,4,5-trimethoxy cinnamic acid and 3,4,5-trimethoxy hydrocinnamic acid can inhibit the generation of melanin, and the cosmetic composition containing the ester compounds can improve the pigmentation in the skin and shows whitening effect without irritation or toxicity, and therefore they can be used for whitening cosmetics.

What is claimed is:

1. An ester compound represented by the following formula 1:

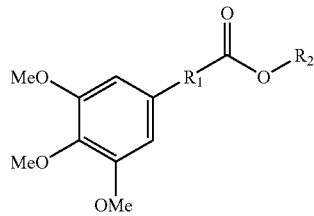

[Formula 1]

wherein $R_1$ is —CH=CH, and $R_2$ is thymyl or carvacryl.

2. A whitening cosmetic composition comprising at least one ester compound of claim 1 with an amount of 0.01~20 wt % to total amount of the cosmetic composition.

* * * * *